United States Patent [19]

Antoniades et al.

[11] Patent Number: 5,019,559

[45] Date of Patent: May 28, 1991

[54] WOUND HEALING USING PDGF AND IGF-II

[75] Inventors: Harry N. Antoniades, Newton; Samuel E. Lynch, Jamaica Plain, both of Mass.

[73] Assignee: President and Fellows of Harvard College, Cambridge, Mass.

[21] Appl. No.: 272,090

[22] Filed: Nov. 16, 1988

Related U.S. Application Data

[63] Continuation of Ser. No. 234,196, Aug. 18, 1988, which is a continuation-in-part of Ser. No. 120,606, Nov. 16, 1987, which is a continuation-in-part of Ser. No. 930,762, Nov. 14, 1986.

[51] Int. Cl.$^5$ ............................................. A61K 37/36
[52] U.S. Cl. ........................................ 514/21; 514/8; 514/12
[58] Field of Search .................................. 514/12

[56] References Cited

U.S. PATENT DOCUMENTS

| | | | |
|---|---|---|---|
| 4,085,204 | 4/1978 | Wacker et al. | 424/101 |
| 4,350,687 | 9/1982 | Lipton et al. | 424/177 |
| 4,479,896 | 10/1984 | Antoniades . | |
| 4,604,234 | 8/1986 | Fujii et al. | 514/2 |
| 4,702,908 | 10/1987 | Thorbecke et al. | 424/88 |
| 4,738,921 | 4/1988 | Belagaje et al. | 435/70 X |
| 4,742,003 | 5/1988 | Derynck et al. | 435/68 |
| 4,745,179 | 5/1988 | Ueda et al. | 530/350 |
| 4,783,524 | 11/1988 | Larsen et al. | 530/399 |
| 4,801,542 | 1/1989 | Murray et al. | 435/70 X |
| 4,861,757 | 8/1989 | Antoniades et al. | 514/21 |

FOREIGN PATENT DOCUMENTS 0267015 4/1987 European Pat. Off.

OTHER PUBLICATIONS

J. of Clin. Inv. 68, 1321-1330 (1981), Zapf et al.
J. of Clin. Endocrinology and Metabolism, 55, 1081-1089 (1982), Merimee et al.
Cell, 31, 8-10 (1982), Czech.
Nature 302, 150-153 (1983), Adams et al.
Febs Letters 89:283 (1987), Rinderknechts et al.
Betsholtz et al., "Growth Factor-Induced Proliferation of Human Fibroblasts in Serum-Free Culture Depends on Cell Density and Extracellular Calcium Concentration," J. of Cellular Physio., 118: 203-210 (1984).
Canalis, "Effect of Platelet-Derived Growth Factor on DNA and Protein Synthesis in Cultured Rat Calvaria," Metabolism, 30:970-975 (1981).
Clemmons et al., "Somatomedin-C and Platelet-Derived Growth factor Stimulate Human Fibroblast Replication," J. of Cellular Physio., 106:361-367 (1981).
Computer print out of various patent abstracts.
Grotendorst, "Can Collagen Metabolism Be Controlled?", J. of Trauma 24:549-552 (1984).
Grotendorst et al., "Molecular Mediators of Tissue Repair," in Soft and Hard Tissue Repair, Hunt et al., eds., Praeger Scientific, 1984, pp. 20-40.
Grotendorst et al., "Stimulation of Granulation Tissue Formation by Platelet-derived Growth Factor in Normal and Diabetic Rats," J. Clin. Invest. 76:2323-2329 (1985).
Hebda, "The Effects of Peptide Growth Factors on Epidermal Outgrowth in an in Vitro Wound Healing Model", J. of Cell Biology, 107: p. 46A (1989).
Heldin etal., "Growth of Normal Human Glial Cells in a Defined Medium Containing Platelet-Derived Growth Factor," Proc. Natl. Acad. Sci. U.S.A., 7: 6611-6615 (1980).
Kabigen Comercial Literature, "Human Cell Growth Factors For Cell Growth and Differentiation".
Lawrence et al., "The Reversal of an Adriamycin Induced Healing Impairment with Chemoattractants and Growth Factors," Ann. Surg., 203: 203:142-147 (1986).
Leal et al., "Evidence That the v-sis Gene Product Transforms by Interaction with the Receptor for Platelet-Derived Growth Factor," Science, 230:327-330 (1985).
Leitzel et al., "Growth Factors and Wound Healing in the Hamster," J. Dermatol. Surg. Oncol., 11:617-621 (1985).
"Lynch et al., Role of Platelet-Derived Growth Factor in Wound Healing: Synergistic Effects With Other Growth Factors," Proc. Natl. Acad. Sci. U.S.A. 84:7696-7700 (1987).
Michaeli et al., "The Role of Platelets in Wound Healing: Demonstration of Angiogenic Activity," Soft and Hard Tissue Repair, Hunt et al., eds., Praeger Scientific, 1984 pp. 380-394.
Mustoe et al., "Accelerated Healing of Incisional Wounds in Rats Induce by Transforming Growth Factor-B," Science, 237:1333-1336 (1987).
Roberts et al., "Type B Transforming Growth Factor: A Bifunctional Regulator of Cellular Growth," Proc. Natl. Acad. Sci. U.S.A., 82:119-123 (1985).
Reddan et al., "Insulin-Like Growth Factors, IGF-1, IGF-2 and Somatomedin C Trigger Cell Proliferation in Mammalian Epithelial Cells Cultured in a Serum-Free Medium," Exp. Cell Res., 142:293-300 (1982).
Rinderknecht et al., "Primary Structure of Human Insulin-Like Growth Factor II," "Proc. Natl. Acad. Sci. U.S.A.," 89:283-286 (1978).
Ross et al., "The Biology of Platelet-Derived Growth Factor," Cell, 46:155-169 (1986).
Schultz et al., "Epithelial Wound Healing Enhanced by Transform Growth Factor," Chemical Abstracts, 106:96915h (1987).

(List continued on next page.)

Primary Examiner—Howard E. Schain

[57] ABSTRACT

Healing an external wound or regenerating bone of a mammal by administering to the mammal a composition containing purified platelet-derived growth factor and purified insulin-like growth factor II.

10 Claims, No Drawings

OTHER PUBLICATIONS

Shipley et al., "Reversible Inhibition of Normal Human Prokeratinocyte by Type B Transforming Growth Factor-Growth Inhibitor in Serum-Free Medium," Cancer Research, 46:2068-2071 (1986).

Sporn et al., Polypeptide Transforming Growth Factors Isolated from Science, 219:1329-1331 (1983).

Sporn et al., "Repair of Tissue in Animal", U.S.S.N. 468,590 Date Filed 2/22/83.

Stiles et al., "Dual Control of Cell Growth by Somatomedins and Platelet Derived Growth Factor," Proc. Natl. Acad. Sci. U.S.A., 76:1279-1283 1979.

Tashjian et al., "Platelet-Derived Growth Factor Stimulates Bone Resorption via a Prostaglandin-Mediated Mechanism," Endocrinology, 111:118-124 (1982).

Van Wyk et al., "Role of Somatomedin in Cellular Proliferation", in *The Biology of Normal Human Growth*, edited by M. Ritzen et al., Raven Press, pp. 223-239 (1981).

WOUND HEALING USING PDGF AND IGF-II

This application is a continuation-in-part of Antoniades et al., entitled "Wound Healing", U.S. Ser. No. 234,196, filed Aug. 18, 1988 which is a continuation-in-part of Antoniades et al., entitled "Wound Healing", U.S. Ser. No. 120,606, filed Nov. 16, 1987, which is a continuation-in-part of Antoniades et al., entitled "Healing External Wounds," U.S. Ser. No. 930,762, filed Nov. 14, 1986, all hereby incorporated by reference and all now abandoned.

BACKGROUND OF THE INVENTION

This invention relates to healing wounds.

Growth factors are polypeptide hormones which stimulate a defined population of target cells. Examples of growth factors include platelet-derived growth factor (PDGF), insulin-like growth factors (IGF-I and II), transforming growth factor beta (TGF-$\beta$), epidermal growth factor (EGF), and fibroblast growth factor (FGF). PDGF is a cationic, heat-stable protein found in the granules of circulating platelets which is known to stimulate in vitro protein synthesis and collagen production by fibroblasts. It is also known to act as an in vitro mitogen and chemotactic agent for fibroblasts, smooth muscle cells, and glial cells.

It has been proposed to use PDGF to promote in vivo wound healing. For example, Grotendorst (1984) J. Trauma 24:549–52 describes adding PDGF to Hunt-Schilling wire mesh chambers impregnated with a collagen gel and implanted in the backs of rats; PDGF was found to increase the amount of new collagen synthesized. However, Leitzel et al. (1985) J. Dermatol. Surg. Oncol. 11:617–22 were unable to accelerate normal wound healing in hamsters using PDGF alone or in combination with FGF and EGF.

Michaeli, et al. (1984) In *Soft and Hard Tissue Repair* (Hunt, T. K. et al., Eds), Praeger Publishers, New York, pp. 380–394, report that application of a partially purified preparation of PDGF obtained from platelet-rich plasma stimulated angiogenesis when implanted in rabbit corneas. Because PDGF is not an angiogenic growth factor the investigators suggested that an unknown factor in their partially purified PDGF preparation was responsible for the angiogenic effect.

SUMMARY OF THE INVENTION

In general, the invention features, in one aspect, healing an external wound in a mammal, e.g., a human patient, by applying to the wound an effective amount of a composition that includes purified PDGF and purified IGF-II. The composition aids in healing the wound, at least in part, by promoting the growth of epithelial and connective tissue and the synthesis of total protein and collagen. Wound healing using the composition of the invention is more effective than that achieved in the absence of treatment (i.e., without applying exogenous agents) or by treatment with purified PDGF alone, or purified IGF-II alone.

In another aspect, the invention features regenerating bone of a mammal, e.g., a human patient, by administering to the patient, preferably by application to the area of injured or depleted bone, an effective amount of a composition that includes purified PDGF and purified IGF-II. The composition aids in regeneration, at least in part, by promoting the growth of connective tissue, bone, and cementum, and by stimulating protein and collagen synthesis. Regeneration using the composition of the invention is more effective than that achieved in the absence of treatment (i.e., without applying exogenous agents) or by treatment with purified PDGF alone, or purified IGF-II alone.

In preferred embodiments of both aspects of the invention, the composition is prepared by combining, in a pharmaceutically acceptable carrier substance, e.g., synthetic polymers or commercially available inert gels or liquids (e.g., methyl cellulose), purified PDGF and IGF-II (both of which are commercially available). Most preferably purified PDGF and IGF-II are combined in a weight-to-weight ratio of between 1:25 and 25:1, preferably between 1:10 and 10:1, and more preferably between 1:2 and 2:1. The purified PDGF may be obtained from human platelets, or solid phase peptide synthesis, or by recombinant DNA technology. The IGF-II may be obtained by recombinant DNA technology or by solid phase peptide synthesis. Thus, by the terms "PDGF" and "IGF-II" we mean platelet-derived, recombinant, and synthesized materials of mammalian, preferably primate, origin; most preferably, the primate is a human, but can also be a chimpanzee or other primate. Recombinant PDGF can be recombinant heterodimer, made by inserting into cultured prokaryotic or eukaryotic cells DNA sequences encoding both subunits of the growth factor, and then allowing the translated subunits to be processed by the cells to form heterodimer. Alternatively, DNA encoding just one of the subunits (preferably the beta or "2" chain) can be inserted into cells, which then are cultured to produce homodimeric PDGF (PDGF-1 or PDGF-2 homodimer).

The term "purified" as used herein refers to PDGF or IGF-II which, prior to mixing with the other, is 95% or greater, by weight, PDGF or IGF-II, i.e., is substantially free of other proteins, lipids, and carbohydrates with which it is naturally associated.

A purified protein preparation will generally yield a single major band on a polyacrylamide gel. Most preferably, the purified PDGF or IGF-II used in the compositions of the invention is pure as judged by amino-terminal amino acid sequence analysis.

The composition of the invention provides a fast, effective method for healing external wounds of mammals, e.g., bed sores, lacerations and burns. The composition enhances connective tissue formation compared to natural healing (i.e. no exogenous agents added) or pure PDGF or IGF-II alone. Unlike pure PDGF alone, the composition promotes about a 90% increase in new connective tissue and about a 50% increase in the growth of epithelial tissue. The epithelial layer obtained is thicker than that created by natural healing, and also contains more epithelial projections connecting it to the new connective tissue; it is thus more firmly bound and protective. In addition, scar formation is minimized.

The composition of the invention also provides a fast, effective method for regeneration of connective tissue and bone of mammals, e.g., humans, with a history of peridontal disease. The composition enhances connective tissue and bone formation compared to natural healing (i.e. no exogenous agents added) or pure PDGF or IGF-II alone.

Other features and advantages of the invention will be apparent from the following description of the preferred embodiments thereof, and from the claims.

DESCRIPTION OF THE PREFERRED EMBODIMENTS

We now describe preferred embodiments of the invention.

External wounds, e.g., bed sores and burns, are treated, and bone and connective tissue regenerated, according to the invention, with PDGF/IGF-II mixtures prepared by combining pure PDGF and IGF-II. IGF-II, also known as multiplication-stimulating activity, is commercially available from ICN Biomedical (Cleveland, Ohio). Purified recombinant PDGF and purified PDGF derived from human platelets are commercially available from PDGF, Inc. (Boston, Mass.), Collaborative Research (Waltham, MA), and Amgen Corp. (Thousand Oaks, Calif.). Purified PDGF can also be prepared as follows:

Five hundred to 1000 units of washed human platelet pellets are suspended in 1M NaCl (2ml per platelet unit) and heated at 100° C. for 15 minutes. The supernatant is then separated by centrifugation and the precipitate extracted twice with the 1M NaCl.

The extracts are combined and dialyzed against 0.08M NaCl-0.01M sodium phosphate buffer (pH 7.4) and mixed overnight at 4° C. with CM-Sephadex C-50 equilibrated with the buffer. The mixture is then poured into a column (5×100 cm), washed extensively with 0.08M NaCl-0.01M sodium phosphate buffer (pH 7.4), and eluted with 1M NaCl while 10 ml fractions are collected.

Active fractions are pooled and dialyzed against 0.3M NaCl-0.01M sodium phosphate buffer (pH 7.4), centrifuged, and passed at 4° C. through a 2.5×25 cm column of Blue Sepharose (Pharmacia) equilibrated with 0.3M NaCl-0.01M sodium phosphate buffer (pH 7.4). The column is then washed with the buffer and partially purified PDGF eluted with a 1:1 solution of 1M NaCl and ethylene glycol.

The partially purified PDGF fractions are diluted (1:1) with 1M NaCl, dialyzed against 1M acetic acid, and lyophilized. The lyophilized samples are dissolved in 0.8M NaCl-0.01M sodium phosphate buffer (pH 7.4) and passed through a 1.2×40 cm column of CM-Sephadex C-50 equilibrated with the buffer. PDGF is then eluted with a NaCl gradient (0.08 to 1M).

The active fractions are combined, dialyzed against 1M acetic acid, lyophilized, and dissolved in a small volume of 1M acetic acid. 0.5 ml portions are applied to a 1.2×100 cm column of Biogel P-150 (100 to 200 mesh) equilibrated with 1M acetic acid. The PDGF is then eluted with 1M acetic acid while 2 ml fractions are collected.

Each active fraction containing 100 to 200 mg of protein is lyophilized, dissolved in 100 ml of 0.4% trifluoroacetic acid, and subjected to reverse phase high performance liquid chromatography on a phenyl Bondapak column (Waters). Elution with a linear acetonitrile gradient (0 to 60%) yields pure PDGF.

PDGF made by recombinant DNA technology can be prepared as follows:

Platelet-derived growth factor (PDGF) derived from human platelets contains two polypeptide sequences (PDGF-1 and PDGF-2 polypeptides; Antoniades, H. N. and Hunkapiller, M. (1983) Science 220:963–965). PDGF-1 is encoded by a gene localized in chromosome 7 (Betsholtz, C. et al., Nature 320:695–699), and PDGF-2 is encoded by the sis oncogene (Doolittle, R. et al. (1983) Science 221:275–277) localized in chromosome 22 (Dalla-Favera, R. (1982) Science 218:686–688). The sis gene encodes the transforming protein of the Simian Sarcoma Virus (SSV) which is closely related to PDGF-2 polypeptide. The human cellular c-sis also encodes the PDGF-2 chain (Rao, C. D. et al. (1986) Proc. Natl. Acad. Sci. U.S.A 83:2392–2396). Because the two polypeptide chains of PDGF are coded by two different genes localized in separate chromosomes, the possibility exists that human PDGF consists of a disulfide-linked heterodimer of PDGF-1 and PDGF-2, or a mixture of the two homodimers (homodimer of PDGF-1 and homodimer of PDGF-2), or a mixture of the heterodimer and the two homodimers.

Mammalian cells in culture infected with the Simian Sarcoma Virus, which contains the gene encoding the PDGF-2 chain, were shown to synthesize the PDGF-2 polypeptide and to process it into a disulfide-linked homodimer (Robbins, K. et al. (1983) Nature 305:605–608). In addition, PDGF-2 homodimer reacts with antisera raised against human PDGF. Furthermore, the functional properties of the secreted PDGF-2 homodimer are similar to those of platelet-derived PDGF in that it stimulates DNA synthesis in cultured fibroblasts, it induces phosphorylation at the tyrosine residue of a 185 kd cell membrane protein, and it is capable of competing with human ($^{125}$I)-PDGF for binding to specific cell surface PDGF receptors (Owen, A. et al. (1984) Science 225:54–56). Similar properties were shown for the sis/PDGF-2 gene product derived from cultured normal human cells (for example, human arterial endothelial cells), or from human malignant cells expressing the sis/PDGF-2 gene (Antoniades, H. et al. (1985) Cancer Cells 3:145–151).

The recombinant PDGF-2 homodimer is obtained by the introduction of cDNA clones of c-sis/PDGF-2 gene into mouse cells using an expression vector. The c sis/PDGF-2 clone used for the expression was obtained from normal human cultured endothelial cells (Collins, T., et al. (1985) Nature 216:748–750).

IGF-II can also be produced by using recombinant DNA technology or solid phase peptide synthesis. Alternatively, IGF-II can be purified from human plasma or conditioned culture media. Rinderknecht et al., Proc. Natl. Acad. Sci. USA 73:2365, (1976); Moses et al., Eur. J. Biochem. 103:387, (1980). Briefly, an acid/ethanol extract is prepared from the acetone powder of a modified Cohn fraction (precipitate B) of human plasma. The acid/ethanol extract is then re-extracted with acetic acid and subjected to Sephadex G-75 and G50 chromatography, SDS-polyacrylamide gel electrophoresis at pH8.6, SE-Sephadex chromatography, and finally polyacrylamide gel electrophoresis at pH 4.3.

Wound Healing

To determine the effectiveness of PDGF/IGF-II mixtures in promoting wound healing, the following experiments were performed.

Young white Yorkshire pigs (Parson's Farm, Hadley, Mass.) weighing between 10 and 15 kg were fasted for at least 6 hours prior to surgery and then anesthetized. Under aseptic conditions, the back and thoracic areas were clipped, shaved, and washed with mild soap and water. The area to be wounded was then disinfected with 70% alcohol.

Wounds measuring 1 cm×2 cm were induced at a depth of 0.5 mm using a modified Castroviejo electrokeratome (Storz, St. Louis, Mo., as modified by Brownells, Inc.). The wounds resulted in complete removal of the epithelium, as well as a portion of the underlying dermis (comparable to a second degree burn injury). Individual wounds were separated by at least 15 mm of unwounded skin. Wounds receiving identical treatment were organized as a group and separated from other groups by at least 3 cm. Wounds receiving no growth factor treatment were separated from wounds receiving such treatment by at least 10 cm.

The wounds were treated directly with a single application of the following growth factors suspended in biocompatible gel: (1) 500 ng pure human PDGF (purified by high performance liquid chromatography) or recombinant PDGF alone; (2) 500 ng pure PDGF in combination with varying amounts of IGF-II; (3) 500 ng pure IGF-II (recombinant, ICN Biomedical, Cleveland, Ohio).

Following wounding, biopsy specimens were taken on day 7. Biopsy specimens for histologic evaluation were taken as wedges approximately 3 mm deep and placed in 10% formalin. Specimens for biochemical analysis and autoradiography were obtained using an electrokeratome. The final dimensions of the specimens were 1.5 mm × 10 mm × 1.5 mm. Three specimens per wound were collected for biochemical analysis, while two specimens per wound collected for autoradiography. Following collection, the specimens were stored in cold Eagle's Modified Essential Medium (EMEM) media supplemented with 10% fetal calf serum. The biopsy specimens were analyzed as follows.

Histologic Evaluation

Histologic specimens were prepared using standard paraffin impregnating and embedding techniques. Four micron sections were made and stained using filtered Harris hemotoxylin and alcoholic eosin; they were then observed under a microscope. All specimens were scored blindly by two investigators at equally distributed points throughout the sections. The widths of the epithelial and connective tissue layers were scored using a grid placed within the ocular of the microscope; the measurement was then converted into millimeters using a micrometer viewed under the same conditions.

Results

The results from histologic evaluation indicated that wounds treated with the combination of purified human PDGF or recombinant PDGF and IGF-II had thicker connective tissue and epithelial layers, and more extensive epithelial projections connecting these layers, than wounds receiving no treatment, pure IGF-II, or pure PDGF alone. There was no evidence of scar formation up to 6 weeks following treatment.

The recombinant purified PDGF-2 homodimer, prepared as described above, was also tested in partial thickness skin wounds alone and in combination with IGF-II. Histological analysis of the six day old wounds indicate that the application of PDGF-2 or IGF-II alone resulted in only slight differences from controls in connective tissue or epidermal morphology. However, when PDGF-2 was combined with IGF-II, the combination produced a significant 90% increase in the width of the new connective tissue layer and a 50% increase in epidermal thickness at seven days postoperatively. The connective tissue of PDGF-2/IGF-II treated wounds had definite areas of polarization of light indicating these wounds contained more mature connective tissue than either wounds receiving PDGF-2 alone IGF-II alone or no treatment.

Thus, application of recombinant PDGF-2 or purified human PDGF produce similar results when applied with IGF-II to the wound healing animal model described above. The combination of recombinant PDGF-2 and IGF-II produces dramatic increases in the number of new fibroblasts and the rate of collagen synthesis, accompanied by hyperplasia of the dermis and epidermis compared to the control animal in the absence of treatment or by treatment with recombinant PDGF-2 or IGF-II alone.

These results indicate that recombinant PDGF-2 homodimer and native purified human PDGF both interact synergistically with IGF-II when applied topically to wounds.

Bone Regeneration

To determine the effectiveness of PDGF/IGF-II preparations in promoting periodontium and/or bone growth, the following experiments can be performed.

Beagle dogs with naturally occurring periodontal disease are selected on the basis of an initial radiographc examination. The teeth which exhibit 30% to 80% bone loss are initially scaled using ultrasonic instruments. Surgical flaps and root planing techniques are then performed, and the experimental teeth treated with a composition containing purified PDGF and IGF-II in a pharmacuetically acceptable carrier substance, e.g., commercially available inert gels, e.g., methyl cellulose. Teeth in the remaining quadrants receive control gel alone, or pure PDGF or IGF-II alone. Block biopsies of the teeth and bone are taken at two weeks postsurgery and prepared for histologic evaluation using standard demineralizing and processing techniques.

Dosage

To determine the appropriate dosage of purified PDGF, the above-described experiments were repeated except that the wounds were treated with 2.5 ng, 5.0 ng, and 10 ng of purified PDGF per square millimeter of wound in combination with 5.0 ng/mm$^2$ of IGF-II dispersed in 30 ml of biocompatible gel. The results showed that optimum effects were produced when the PDGF content was 5.0 ng/mm$^2$ or higher.

To determine the appropriate dosage of pure PDGF plus IGF-II, combinations in which the weight to weight ratio of PDGF to IGF-II ranged from 1:25 to 25:1were evaluated as described above. Optimum results were achieved with a ratio of between 1:2 and 2:1.

Other Embodiments

Other embodiments are within the following claims. For example, the combination of IGF-II and PDGF is useful for promoting bone growth and/or periodontum growth.

We claim:

1. A method for healing an external wound of a mammal comprising applying to said wound a wound-healing amount of a composition comprising purified platelet-derived growth factor and purified insulin-like growth factor II.

2. A method for regenerating bone of a mammal comprising administering to said mammal a wound-healing amount of a composition comprising purified platelet-derived growth factor and insulin-like growth factor II.

3. The method of claim 1 or claim 2 wherein the weight to weight ratio of said platelet-derived growth factor to said insulin-like growth factor II in said composition is between 1:25 and 25:1.

4. The method of claim 3 wherein said ratio is between 1:10 and 10:1.

5. The method of claim 4 wherein said ratio is between 1:2 and 2:1.

6. A wound healing and bone regenerating composition comprising purified platelet-derived growth factor and purified insulin-like growth factor II, in a weight to weight ratio of 1:25 to 25:1.

7. The composition of claim 6 wherein said ratio is between 1:10 and 10:1.

8. The composition of claim 7 wherein said ratio is between 1:2 and 2:1.

9. A method for preparing a composition for healing wounds, comprising mixing purified platelet-derived growth factor and purified insulin-like growth factor II in a weight to weight ratio of between 1:25 and 25:1.

10. A method for promoting bone or periodontum growth comprising applying to said bone or periodontum a growth promoting amount of a composition comprising purified platelet-derived growth factor and purified insulin-like growth factor II.

* * * * *

UNITED STATES PATENT AND TRADEMARK OFFICE
CERTIFICATE OF CORRECTION

PATENT NO. : 5,019,559

DATED : May 28, 1991

INVENTOR(S) : Harry N. Antoniades and Samuel E. Lynch

It is certified that error appears in the above-identified patent and that said Letters Patent is hereby corrected as shown below:

On the title page, item [73] in the "Assignee", insert
--Institute of Molecular Biology, Inc.;

Item [56] Under "Foreign Patent Documents", add --0312208 4/19/89 Europe --;

Item [56] Under "Other Publications", second column, at the bottom where it says "(List continued on next page.)", add the following to the next page as follows:

--Shipley et al., "Reversible Inhibition of
Normal Human Prokeratinocyte by Type B
Transforming Growth Factor-Growth Inhibitor
in Serum-Free Medium," Cancer Research,
46:2068-2071 (1986);

--Sporn et al., Polypeptide Transforming
Growth Factors Isolated from Bovine Sources
and Used for Wound Healing in vivo," Science,
219: 1329-1331 (1983);

--Sporn et al., "Repair of Tissue in Animal",
U.S.S.N. 468,590, Dated Filed 2/22/83;

--Stiles et al., "Dual Control of Cell Growth
by Somatomedins and Platelet Derived Growth
Factor," Proc. Natl. Acad. Sci. USA, 76:1279-1283 (1979);

--Tashjian et al., "Platelet-Derived Growth
Factor Stimulates Bone Resorption via a
Prostaglandin-Mediated Mechanism,"
Endocrinology, 111:118-124 (1982);

UNITED STATES PATENT AND TRADEMARK OFFICE
CERTIFICATE OF CORRECTION

PATENT NO. : 5,019,559

DATED : May 28, 1991

INVENTOR(S) : Harry N. Antoniades, et al.

It is certified that error appears in the above-identified patent and that said Letters Patent is hereby corrected as shown below:

--Van Wyk et al., "Role of Somatomedin in Cellular Proliferation in The Biology of Normal Human Growth, edited by M. Ritzen et al. Raven press pp. 223-239 (1981); --

Signed and Sealed this

Twenty-third Day of March, 1993

*Attest:*

STEPHEN G. KUNIN

*Attesting Officer*   *Acting Commissioner of Patents and Trademarks*